United States Patent [19]

Fly et al.

[11] 4,120,191

[45] Oct. 17, 1978

[54] QUALITY CONTROL FOR FIBROUS MATS

[75] Inventors: James Alan Fly, Conroe, Tex.; Robert O. Slonaker, Pataskala, Ohio

[73] Assignee: Owens-Corning Fiberglas Corporation, Toledo, Ohio

[21] Appl. No.: 823,255

[22] Filed: Aug. 10, 1977

[51] Int. Cl.² ............................................. G01N 19/02
[52] U.S. Cl. ............................................................ 73/9
[58] Field of Search ................................. 73/9, 7, 159

[56] References Cited

U.S. PATENT DOCUMENTS 3,643,490   12/1977   Hertel ........................................ 73/9

Primary Examiner—Donald O. Woodiel
Attorney, Agent, or Firm—Ronald C. Hudgens; Philip R. Cloutier; Ted C. Gillespie

[57] ABSTRACT

A testing method and apparatus for measuring the frictional force between abrasive surfaces and a fibrous mat are disclosed. The measure of the frictional force gives an indication of the looseness of the bonding of the fibers on the surface of the mat.

5 Claims, 3 Drawing Figures

QUALITY CONTROL FOR FIBROUS MATS

This invention relates to the production of fibrous mats, particularly mats made from fibrous mineral material. The mats can be either chopped strand mat or continuous strand mat. Such mats are commonly made by the depositing of fibrous material onto conveyor surfaces and by bonding the fibers together with a binder. Binders are commomly applied in a powdered form and the mat having binder applied is then taken through a curing process. During the curing process the fibers are bonded together where they intersect to form a mat with a certain amount of structural rigidity.

Occassionally in mat producing processes, problems in binder application and binder curing result in fibrous mats having poorly bonded or improperly bonded fibers, particularly on the surfaces of the mats. Such mats are often unacceptable in the market place, and result in wasted production.

Heretofore, there has been no objective means of measuring the quality of the bonding of the fibers at the surface of a fibrous mat. The test commonly used was either a visual inspection or a subjective manual inspection.

There has now been discovered a method and apparatus for objectively testing the looseness of the fibers on the surface of a fibrous bonded mat. The test comprises the measurement of the frictional force between the mat and an abrasive surface. The surface is moved relative to the mat, and it can be urged into contact with mat with a uniform or predetermined force. The mat can be placed in between two abrasive surfaces in a laminated construction in order to test the looseness of both the top and bottom surface of the mat. The frictional force can be measured with a strain gauge.

According to this invention there is provided an apparatus for measuring the looseness of a fibrous mat comprising an abrasive surface, means for urging the surface into contact with the mat, means for moving the surface with respect to the mat, and means for measuring the frictional force between the surface and the mat. The surface can be moved at a predetermined velocity with respect to the mat. The apparatus for measuring the looseness of the fibrous mat according to this invention can comprise a pair of abrasive surfaces, each of the surfaces contacting one side of the mat. Where there is more than one abrasive surface, the force measured can be the total frictional force between the mat and the surfaces. The means for measuring the frictional force can be a strain gauge. Alternatively, there can be individual measurements of the force between the mat and each abrasive surface. The abrasive surface can be comprised of a sandpaper surface. The measuring of the looseness of the fibrous mat according to this invention can be accomplished while the mat is traveling on a conveyor.

Also, according to this invention there is provided a method for measuring the looseness of a fibrous mat comprising contacting a mat with an abrasive surface at a predetermined force between the mat and the abrasive surface, moving the abrasive surface with respect to the mat, and measuring the frictional force between the abrasive surface and the mat. The surface can be moved at a predetermined velocity with respect to the mat. The method of measuring the looseness of the fibrous mat according to this invention can comprise urging a pair of abrasive surfaces into contact with the mat at a predetermined force, moving one of the abrasive surfaces with respect to the mat, and measuring the frictional force between the mat and the abrasive surfaces. The frictional force can be measured with a strain gauge. The measuring of the looseness of the fibrous mat according to this invention can be accomplished while the mat is traveling on a conveyor.

The method and apparatus of this invention are particularly suitable for the measuring of the looseness of fibrous mats comprising glass fibers.

Figure 1:
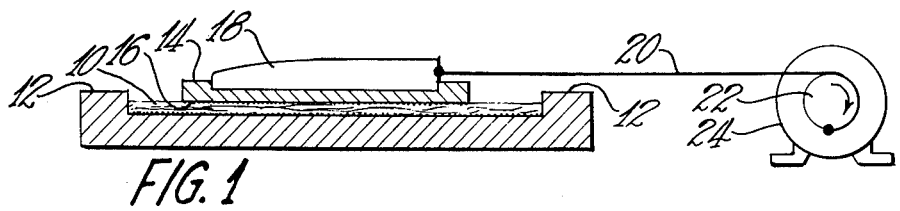
FIG. 1 is an elevational view of apparatus, according to the principles of the invention, in which an abrasive plate is adapted to be in contact with a stationary mat.

Referring now to FIG. 1, there is shown fibrous mat 10 which is anchored in place by anchor means 12 which can be any suitable means for anchoring the mat. Placed on top of the mat is plate member 14. The bottom of the plate member is comprised of abrasive surface 16. The plate member with its abrasive surface rests on the mat in such a manner that relative movement between the plate member and the mat causes friction between the abrasive surface and the mat. The abrasive surface can be comprised of a #80 grit sandpaper, although other types and grades of abrasive surfaces can be utilized.

Attached to the plate member is strain gauge 18 which is used to measure the frictional force between the abrasive surface and the mat. When the abrasive surface is moving with respect to the mat, the force measured is the dynamic frictional force. The strain gauge is connected to the plate member so that a force applied to the strain gauge is transmitted to the abrasive surface. A strain gauge which is suitable for use according to this invention is a "Chatillon" strain gauge (Model DPP-10). The weight of the strain gauge and the plate member push the abrasive surface down onto the mat. For different forces to be applied to the abrasive surface, additional weight can be added to the plate member, or other suitable biasing means can be employed. When there is relative movement between the mat and the abrasive surface, and when the abrasive surface is urged toward the mat to create a frictional force, there is said to be "frictional engagement" between the abrasive surface and the mat.

The strain gauge is connected by cable 20 to shaft 22 of motor 24. The motor can be any conventional motor which can wind the cable on the shaft at a constant rate. The force of the cable winding on the shaft pulls the strain gauge toward the motor. The force on the strain gauge is applied through the plate member to the abrasive surface. Since the mat is anchored, there is relative movement between the abrasive surface and the mat. And, since the abrasive surface is in contact with the mat, there is a frictional force between the abrasive surface and the mat. The reading on the strain gauge measures this frictional force, which is the resistance of the mat to the force applied by the winding of the cable on the motor. It is the looseness or lack or looseness of the fibers on the surface of the mat which provides variations in the frictional force. The greater the degree of looseness in the surface of the mat, the lower the frictional force will be between the abrasive surface and the mat.

Figure 2:
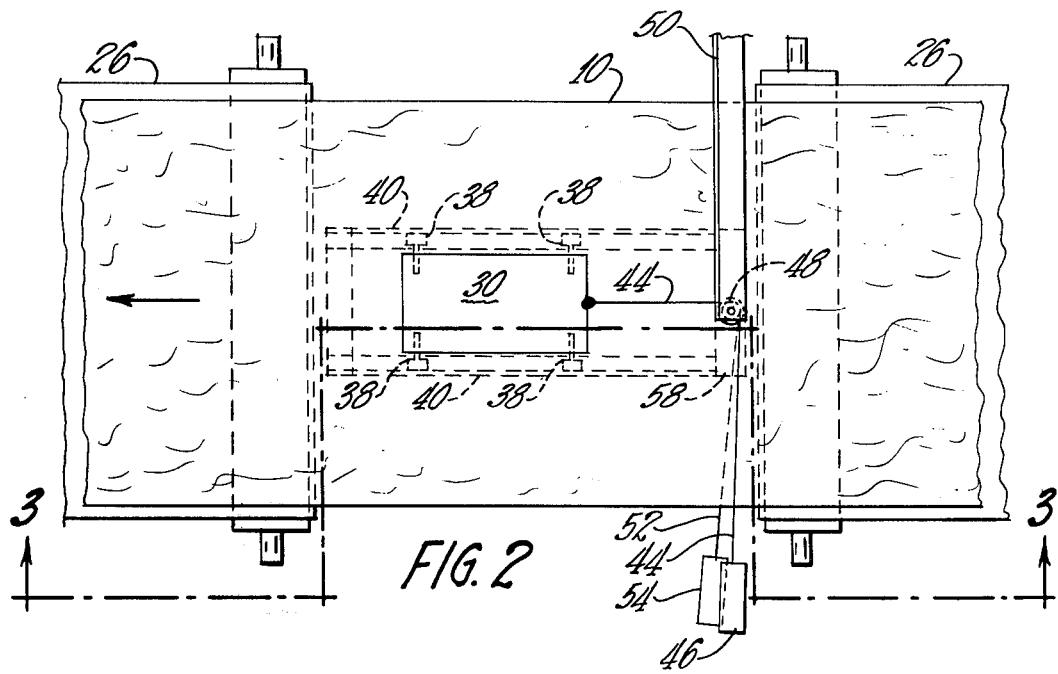
FIG. 2 is a plan view of apparatus for measuring the looseness of both surfaces of a fibrous mat which is traveling on a conveyor.
Figure 3:
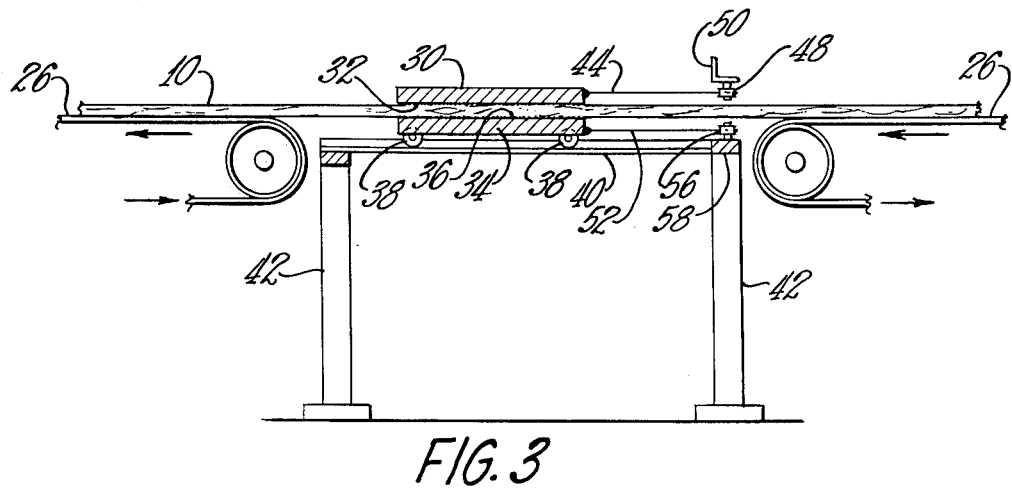
FIG. 3 is a sectional elevation taken along the line 3—3 of FIG. 2.

Referring now to FIGS. 2 and 3, the mat can be seen to be traveling on conveyors 26 in the direction shown by the arrow. Top plate member 30 rests on the mat. The top plate member has abrasive surface 32 which contacts the mat. The mat itself rests on bottom plate member 34 which has abrasive surface 36. The bottom plate member can be adapted with rollers 38 or other suitable antifriction means to slide freely along a line in the direction of movement of the conveyor. The rails can be mounted on any suitable support means such as support members 42.

Cable 44 is rigidly fixed to the top of the plate member and is adapted to transmit the frictional force on the top abrasive surface to upper surface strain gauge 46, which can be fixed with respect to ground. The upper cable can be mounted to make a turn on pulley member 48 mounted on support bar 50. The drag force between the upper surface of the mat and the top plate abrasive surface will be transmitted through the top cable and will register on the upper surface strain gauge. The top plate member is restrained from moving downstream with the mat by the restraint applied by the top cable.

The bottom plate member is tied by means of bottom cable 52 to bottom surface strain gauge 54, which can be rigidly mounted. The bottom cable can be adapted to travel around suitable pulley member 56, which can be mounted on cross member 58, which is itself mounted on the support members. The weight of the top plate member and the weight of the mat urge the mat down onto the bottom abrasive surface, and this creates a frictional force between the bottom surface of the moving mat and the bottom plate abrasive surface. The bottom plate member would otherwise be free to move downstream with the fibrous mat but it is held in place by the bottom cable. The frictional force between the mat and the abrasive surface of the bottom plate is transmitted through the bottom cable to the bottom surface strain gauge. Thus it can be seen that the frictional force between the mat and both the top and the bottom abrasive surfaces can be measured independently and continuously. This provides a continuous measure of the quality of the mat.

It is to be understood that the apparatus of this invention can be adapted to be applied to a mat which is in a vertical rather than a horizontal position.

It will be evident from the foregoing that various modifications can be made to the present invention. Such, however, are considered as being within the scope of the invention.

What is claimed is:

1. Apparatus for measuring the looseness of a fibrous mat comprising:
    (a) an abrasive surface;
    (b) means for urging said abrasive surface into contact with said mat with a predetermined force;
    (c) means for moving said abrasive surface with respect to said mat; and
    (d) a strain gauge for measuring the frictional force between said abrasive surface and said mat.

2. The apparatus of claim 1 comprising:
    (a) a pair of abrasive surfaces, each abrasive surface contacting one side of said mat;
    (b) means for urging said abrasive surfaces into contact with said mat with a predetermined force;
    (c) means for moving one of said abrasive surfaces with respect to said mat; and,
    (d) a strain gauge for measuring the frictional force between said mat and said abrasive surfaces.

3. The apparatus of claim 2 in which said abrasive surface comprises a sandpaper surface.

4. The method for measuring the looseness of a fibrous mat comprising:
    (a) contacting said mat with an abrasive surface at a predetermined force between said mat and said abrasive surface;
    (b) moving said abrasive surface with respect to said mat; and,
    (c) measuring the frictional force between said abrasive surface and said mat with a strain gauge.

5. The method of claim 4 comprising:
    (a) urging a pair of abrasive surfaces into contact with said mat with a predetermined force;
    (b) moving one of said abrasive surfaces with respect to said mat; and,
    (c) measuring the frictional force between said mat and said abrasive surfaces with a strain gauge.